United States Patent [19]

Morgan, Jr.

[11] 3,972,940
[45] Aug. 3, 1976

[54] CATALYST SUSPENSION FOAMING INHIBITION

[75] Inventor: Jewel C. Morgan, Jr., Cantonment, Fla.

[73] Assignee: Monsanto Company, St. Louis, Mo.

[22] Filed: Dec. 19, 1974

[21] Appl. No.: 534,386

[52] U.S. Cl.............................. 260/583 K; 260/690
[51] Int. Cl.².......................................... C07B 1/00
[58] Field of Search............... 252/477 Q, 361, 358; 260/583 K

[56] References Cited
UNITED STATES PATENTS

| | | | |
|---|---|---|---|
| 3,551,495 | 12/1970 | Alt et al. | 260/583 K UX |
| 3,673,251 | 6/1972 | Frampton et al. | 260/583 K X |
| 3,859,329 | 1/1975 | Lambert et al. | 260/583 K X |

FOREIGN PATENTS OR APPLICATIONS

| | | | |
|---|---|---|---|
| 246,665 | 8/1960 | Australia | 260/583 K |
| 151,919 | 6/1953 | Australia | 252/358 |
| 658,494 | 10/1951 | United Kingdom | 252/358 |

OTHER PUBLICATIONS

Perry, "Chem. Engr. Handbook," p. 515, 3rd Ed. 1950.

*Primary Examiner*—Allen B. Curtis
*Attorney, Agent, or Firm*—Thomas Y. Awalt, Jr.; George R. Beck

[57] ABSTRACT

A process in which a Raney nickel or Raney cobalt hydrogenation catalyst is suspended in an aqueous liquid for feeding of the catalyst into a reaction medium in which an amine is prepared by continuous catalytic hydrogenation of a nitrile reactant is improved by including in the aqueous liquid a portion of the reaction medium containing an amount of the amine sufficient to substantially inhibit foaming of the catalyst suspension.

10 Claims, No Drawings

CATALYST SUSPENSION FOAMING INHIBITION

BACKGROUND OF THE INVENTION

In typical continuous processes utilizing a Raney nickel or Raney cobalt hydrogenation catalyst, the rate at which the catalyst is fed into the reaction medium must be carefully controlled. Active catalysts of that type are pyrophoric, however, and are therefore normally kept out of contact with air by transporting and storing the catalyst in a relatively inert liquid. Hence in some of the aforementioned processes, the rate at which the catalyst is fed into the reaction medium is desirably controlled by suspending the catalyst is such a liquid so as to disperse the catalyst substantially uniformly through the liquid in a known concentration of catalyst per unit volume of the suspension, and then controlling the volumetric flow rate of the suspension into the reaction mixture. Examples of processes in which the catalyst feed rate may be conveniently controlled in this way are described in U.S. Pat. No. 3,821,305 issued June 28, 1974 to G. Bartalini et al., the disclosure of which is incorporated herein by reference, and in U.S. Pat. No. 3,056,837 issued Oct. 2, 1962 to W. M. Steeman.

In processes such as that of U.S. Pat. No. 3,821,305 in which the reaction medium contains water, it may be also convenient to uniformly suspend the catalyst in water in the relative proportions in which the catalyst and water are desirably fed into the reaction medium and then control the feed rate of both water and catalyst by controlling only the volumetric feed rate of the resulting catalyst-in-water suspension. One difficulty encountered in use of a suspension of active Raney nickel or Raney cobalt catalyst in water, however, is that since such catalysts have relatively high densities, maintaining even very finely divided particles of the catalyst suspended in substantially uniform dispersion throughout the water typically requires an essentially constant and relatively vigorous stirring or other agitation of the suspension and, for reasons not fully understood, such agitation normally results in substantial foaming of the suspension. In many cases the foaming tendency is so severe that it presents a significant danger of loss of the pyrophoric catalyst by overflow from catalyst feed tanks. A technique for inhibiting such foaming is therefore very desirable and it is an object of this invention to provide such a technique for improvement of certain catalytic hydrogenation processes that involve suspending of a Raney nickel or Raney cobalt catalyst in an aqueous liquid for feeding of the catalyst into the hydrogenation reaction medium. Other objects of the invention will be apparent from the following disclosure in which all percentages are by weight except where otherwise noted.

SUMMARY OF THE INVENTION

It has now been discovered that foaming of a suspension of a solid particulate Raney nickel or Raney cobalt hydrogenation catalyst in an aqueous liquid can be very substantially inhibited by including an amine in said liquid, and that in a process for preparation of an amine by catalytic hydrogenation of a nitrile reactant, this can be generally accomplished most conveniently by merely including in the aqueous liquid a portion of the reaction medium comprising the amine product of that process. Accordingly, and more specifically in a process in which an amine is prepared by continuously hydrogenating a nitrile reactant in a liquid reaction medium comprising the amine and said reactant in a reaction zone maintained under hydrogenation conditions including a temperature of at least 60°C., molecular hydrogen and said reactant are continuously fed into said zone, a solid particulate Raney nickel or Raney cobalt hydrogenation catalyst is fed into said zone by suspending the catalyst in an aqueous liquid at a temperature below 50°C. and then feeding the resulting suspension into said zone, and said reaction medium and catalyst are withdrawn from said zone at relative rates that maintain essentially constant the proportions of reactant, catalyst and amine in said zone, the present invention provides the improvement which comprises including in said aqueous liquid a portion of the withdrawn reaction mixture containing an amount of said amine sufficient to substantially inhibit foaming of said suspension. Carrying out of this invention not only substantially inhibits foaming of the suspension but also provides the further advantage of doing so without introduction of any extraneous substance into the hydrogenation reaction mixture. Also provided by the invention are other advantages including decreased potential for accidental loss of catalyst, increased ease of handling and metering flow of the catalyst suspensions and improved catalytic hydrogenation process control.

DETAILED DESCRIPTION OF THE INVENTION

The catalysts referred to herein are Raney nickel and Raney cobalt catalysts having hydrogenation activity for use in hydrogenation of various nitrile reactants such as, for example, adiponitrile or $\epsilon$-aminocapronitrile, to amines such as hexamethylenediamine. Either the Raney nickel or the Raney cobalt may optionally include a minor amount of one or more other metals such as, for example, a few percent by weight of chromium. These catalysts are normally solid and are further referred to herein as being particulate, meaning that such catalysts, as employed in the present invention, are of particle sizes such that the catalyst can be suspended in water or other aqueous liquids having densities on the order of that of water by stirring or other agitation of the liquid containing such a catalyst. Exemplary catalyst particles have diameters between about 10 and 200 microns, although considerably larger or somewhat smaller particle sizes may be employed.

Also as used herein, terms such as "suspending" of the catalyst and the resulting catalyst "suspension" refer to dispersions of the catalyst particles throughout an aqueous liquid in any degree of uniformity that is gravitationally decreased at a significant rate in the absence of a counteracting force such as stirring or other agitation of the liquid. Hence as used herein those terms are applicable to relatively unstable suspensions as distinguished from suspensions in which finely divided (e.g. colloidal) particles are maintained in suspension in a liquid indefinitely by Brownian movement. In some preferred embodiments of the invention, the suspension contains between about 5% and about 25% of the catalyst by weight of the aqueous liquid in which it is suspended, although higher or lower catalyst concentrations may be used if desired.

The aqueous liquid in which the catalyst is suspended in practice of the invention generally contains at least about 10%, typically at least about 30% and in many cases at least about 50% water by weight. This liquid is employed for storage and transport of the catalyst prior to use of the catalyst in the desired hydrogenation reaction and hence is preferably one in which the hydrogenation activity of the catalyst is not lowered at a substantial rate which, as used herein, means a daily (24 hour) rate greater than one percent of the hydrogenation activity of the catalyst as conventionally measured, e.g. in standard cubic centimeters of hydrogen per gram of catalyst. This may require in some instances that the aqueous liquid be sparged or blanketed with hydrogen, and it is also generally desirable that substantially all (at least about 90%, preferably at least about 95% and even more preferably at least about 98%) of the aqueous liquid is made up of water and the amine hydrogenation product, although in many useful embodiments of the invention the aqueous liquid may contain substantial proportions of other constituents such as low molecular weight alcohols, e.g. a $C_1$–$C_4$ alkanol such as ethanol.

The amines prepared by the process improved by this invention and employed in practice of the invention are typically non-olefinic (i.e., substantially completely devoid of olefinic unsaturation) and also typically hydrocarbylamines by which is meant amines that, aside from their amine groups, are essentially completely composed of hydrocarbon radicals. They may be non-olefinically unsaturated as in, for example, aromatic amines such as a para-phenylenediamine or a xylylenediamine, but in many embodiments of the invention the amine is a paraffinic amine by which is meant a compound consisting of one or more amino groups and one or more completely saturated hydrocarbon radicals. Most commonly they are primary amines but secondary and tertiary amines are also useful in practice of the invention. Especially good results are achieved when the amine is a diamine but monoamines, triamines, tetraamines, etc. are also within the scope of the invention. In typical embodiments the amine contains from 2 to 14 carbon atoms, and in especially preferred embodiments the amine is a $C_2$–$C_{14}$ paraffinic diamine which may be cyclic such as, for example, a cyclohexanebis-(methylamine) or bis(4-aminocyclohexyl)methane, or it may be of the straight-chain variety including particularly, for example, the $C_4$–$C_{12}$ $\alpha,\omega$-polymethylenediamines such as tetramethylenediamine, hexamethylenediamine, decamethylenediamine or dodecamethylenediamine, or they may be of the branched-chain variety including, for example, similar $\alpha,\omega$-polymethylenediamines having a lower (e.g. $C_1$–$C_4$) alkyl substituent on at least one of the carbon atoms in the polymethylene chain. Also typically, the amine employed in the present invention has a molecular weight not substantially greater than about 200, but may have a somewhat higher molecular weight in some instances. Especially good results are achieved when the amine is a $C_4$–$C_8$ $\alpha,\omega$-polymethylenediamine and particularly hexamethylenediamine.

As aforesaid, the amount of the amine that is used is at least an amount sufficient to substantially inhibit foaming of the catalyst suspension. The sufficiency of a given amount of the amine to substantially inhibit such foaming is normally easily ascertained, e.g. by visual observation of the foaming-suppression effects of gradual addition of a portion of the withdrawn reaction medium containing that amount of the amine to an aqueous liquid that has been foaming as a result of stirring or other agitation to suspend a Raney nickel or Raney cobalt catalyst in that liquid. For best results when the amine is a $C_2$–$C_{14}$ paraffinic diamine, it is usually desirable that the amount of the amine in the aqueous liquid be greater than about 5% and in most cases at least about 10% by weight of the liquid which, in this application, is considered exclusive of the weight of any solid catalyst present in the liquid. Substantially greater amounts of the amine may not be necessary for adequate foaming control, but amounts up to about 50%, 70% or even about 90% by weight of the liquid can be ordinarily used without significant disadvantage. Of course the concentration of the amine in the aqueous liquid will not be greater than its concentration in the portion of the withdrawn reaction medium that is included in that liquid and accordingly, the concentration of the amine in the withdrawn reaction medium has some bearing on the quantity of withdrawn reaction medium that is used to provide the amount of the amine employed for foaming inhibition. To illustrate the degree to which the quantity of withdrawn reaction medium included in the aqueous liquid in practice of the invention may be dependent on the concentration of the amine in that portion of the withdrawn reaction medium, it is pointed out that in hydrogenation processes such as that of U.S. Pat. No. 3,821,305, the amine may constitute as much as 90% or more of the reaction medium, but in other processes within the scope of the invention the amine may constitute a much lower proportion of the reaction medium, e.g. as little as 20–30% thereof or even less. In further clarification of such terms as used herein, it should be noted that concentrations of an amine in a portion of the reaction medium are expressed on a basis exclusive of the weight of any solid catalyst present in that portion of the medium, and a "portion of said withdrawn reaction medium" is intended to mean an essentially representive portion of said withdrawn reaction medium as opposed to a fraction thereof in which the weight ratio of nitrile reactant to amine product differs greatly (i.e., by more than about 50%) from the corresponding ratio in said withdrawn reaction medium, e.g. as a result of distillation that separates such a fraction from such withdrawn reaction medium.

In an especially preferred embodiment of the invention, catalyst withdrawn from the reaction zone is washed with water to remove adhering reaction medium, and a substantial part (e.g. at least about 25% and typically at least about 50%) of the portion of withdrawn reaction medium that is included in the aforementioned aqueous liquid is included therein by including the resulting catalyst washings containing water and withdrawn reaction medium in said liquid. In this embodiment, two important advantages are realized. First, withdrawn reaction medium washed from the withdrawn catalyst is recycled into the reaction zone without need for separation from the water used in washing of the catalyst and second, product amine in the washings is used to inhibit foaming of the catalyst suspension without need for an interim separation from the water or nitrile reactant in the washings. In fact, in some embodiments of processes like that of U.S. Pat. No. 3,821,305, it can be most convenient for the major part or even essentially all of the aqueous liquid used in feeding of catalyst into the reaction zone to be composed of such withdrawn catalyst washings. In such embodiments, the catalyst washings normally contain enough of the amine to adequately inhibit foaming of the suspension but if it is desired to lower the proportion of water fed into the reaction zone together with the suspended catalyst, this can be accomplished by using only a part of such washings together with withdrawn reaction medium not washed from withdrawn catalyst to make up the aqueous liquid in which catalyst is suspended for feeding into the reaction zone.

Conditions under which the amines referred to herein can be prepared by hydrogenation of a nitrile reactant in the presence of a Raney nickel or Raney cobalt hydrogenation catalyst are well known in the art. Illustrative conditions are described in the aforementioned U.S. Pat. Nos. 3,821,305 and 3,056,837. In general, those conditions include temperatures from 60°C. to about 100°C., pressures from about 20 to about 50 or even up to about 100 atmospheres and typically fairly carefully controlled proportions of the amine product, nitrile reactant, catalyst, water and other reaction medium constituents which may include, for example, an alkali metal hydroxide and/or an inert diluent such as ethanol or other low molecular weight monoalkanol. In practice of the invention, reaction medium is withdrawn continuously and catalyst is withdrawn either continuously or semi-continuously (e.g. at least once a day) from the reaction zone at rates such that the proportions of reactant, catalyst and amine in the reaction zone are maintained essentially constant, by which is meant sufficiently constant to provide continuous production of the amine with a molar selectivity, based on converted nitrile reactant, that does not normally very substantially (e.g. more than about 1%) as a result of variations of such proportions of reactant, catalyst and amine.

EXAMPLE I

One part by weight of a solid particulate Raney nickel catalyst containing about 3% by weight of chromium and finely divided such that 100% of the catalyst particles had diameters smaller than 65 microns and 90% by weight had diameters of at least 15 microns was suspended in and maintained substantially uniformly dispersed throughout nine parts by weight of a 35°C. aqueous liquid containing 75% water by mechanical agitation in a catalyst feed tank continuously sparged with hydrogen and maintained under a total pressure of 1.03 atmospheres. The resulting catalyst suspension was then essentially continuously fed at a desired rate into a reaction zone in which adiponitrile was continuously catalytically hydrogenated to prepare hexamethylenediamine (HMD) essentially as described in U.S. Pat. No. 3,821,305, by controlling the volumetric flow rate of the substantially uniform suspension of the catalyst from the feed tank into the reaction zone. Molecular hydrogen, adiponitrile and caustic soda were also continuously fed into the reaction zone which was maintained under hydrogenation conditions including a temperature between 70° and 80°C. and a pressure of 34 atmospheres. Reaction medium and catalyst were withdrawn from the reaction zone at relative rates such that the proportion of catalyst to liquid reaction medium in the reaction zone was maintained essentially constant at approximately 1:5 weight, the concentrations of HMD and water in the liquid reaction medium were maintained essentially constant at 94.6% and 4%, respectively, and the weight ratio of nitrile reactant to HMD in the liquid reaction medium was maintained essentially constant at a nitrile reactant concentration below 1%. Under those conditions adiponitrile was converted to HMD with a molar selectivity in excess of 98.5%. Catalyst withdrawn from the reaction zone was washed with water to remove adhering liquid reaction medium and the resulting washings were included in the aqueous liquid in which catalyst was suspended for feeding into the reaction zone. The quantity of withdrawn reaction medium thereby included in the aqueous liquid was such that 24.8% of the liquid was HMD and under those conditions, there was essentially no foaming of the catalyst suspension in the feed tank.

EXAMPLE II

When Example I is repeated except that a smaller portion of the washings is included in the aqueous liquid and the remainder of the aqueous liquid is made up with water such that the concentrations of water and HMD in the aqueous liquid are 89.9% and 10%, respectively, the results are the same, i.e., there is essentially no foaming of the catalyst suspension in the feed tank.

EXAMPLES III – IV

When Example I is repeated three times except that in each case a smaller portion of the washings is included in the aqueous liquid and the remainder of the aqueous liquid is made up with withdrawn reaction medium not washed from withdrawn catalyst such that the concentrations of water and HMD in the aqueous liquids are as shown immediately hereinafter, the results are the same, i.e., there is essentially no foaming of any of the catalyst suspensions in the feed tank.

Example III — 60% water and 39.7% HMD;
Example IV — 35% water and 64.5% HMD;
Example V — 15% water and 84.3% HMD.

Comparative Example

When Example I is repeated except that the catalyst is suspended in essentially pure water containing no HMD or other amine, the agitation required to suspend and disperse the catalyst throughout the water results in such severe foaming of the suspension that large quantities of the catalyst are lost through the catalyst feed tank vent system.

I claim:

1. In a process in which an amine is prepared by continuously hydrogenating a nitrile reactant in a reaction medium comprising the amine and said reactant in a reaction zone maintained under hydrogenation conditions including a temperature of at least 60°C., molecular hydrogen and said reactant are continuously fed into said zone, a solid particulate Raney nickel or Raney cobalt hydrogenation catalyst is fed into said zone by suspending the catalyst in an aqueous liquid at a temperature below 50°C. and then feeding the resulting suspension into said zone, and said reaction medium and catalyst are withdrawn from said zone at rates that maintain essentially constant the proportions of reactant, catalyst and amine in said zone, and the amine is subsequently separated from the remainder of the reaction medium the improvement which comprises including in said aqueous liquid, prior to feeding the resulting suspension into said zone a portion of said withdrawn reaction medium containing an amount of said amine sufficient to substantially inhibit foaming of said suspension.

2. A process improvement according to claim 1, wherein the amine is $C_2$–$C_{14}$ paraffinic diamine and said aqueous liquid is at least about 10% water by weight.

3. A process improvement according to claim 2, wherein said amount is at least about 10% by weight of said aqueous liquid.

4. A process improvement according to claim 3, wherein at least about 90% by weight of said aqueous liquid is water and said diamine.

5. A process improvement according to claim 2, wherein the amine is $C_4$–$C_{12}$ $\alpha,\omega$-polymethylenediamine and said aqueous liquid is at least about 50% water by weight.

6. A process improvement according to claim 5, wherein said amount is at least about 10% by weight of said aqueous liquid, and at least about 95% by weight of said aqueous liquid is water and said polymethylenediamine.

7. A process improvement according to claim 2, wherein said aqueous liquid is at least about 30% water by weight.

8. A process improvement according to claim 7, wherein said amount is at least about 10% by weight of said aqueous liquid and the amine is hexamethylenediamine.

9. A process improvement according to claim 8, wherein at least about 98% by weight of said aqueous liquid is water and hexamethylenediamine.

10. A process improvement according to claim 8, wherein withdrawn reaction medium is washed from said withdrawn catalyst with water, and a substantial part of said portion of withdrawn reaction medium is included in said aqueous liquid by including the resulting washings containing water and withdrawn reaction medium in said aqueous liquid.

* * * * *